United States Patent [19]
Atala

[11] Patent Number: 6,048,330
[45] Date of Patent: Apr. 11, 2000

[54] SYSTEMS AND METHODS FOR PROMOTING TISSUE GROWTH

[75] Inventor: Anthony Atala, Weston, Mass.

[73] Assignee: Children's Medical Center Corporation, Boston, Mass.

[21] Appl. No.: 08/850,545

[22] Filed: May 2, 1997

Related U.S. Application Data

[63] Continuation-in-part of application No. 08/326,711, Oct. 20, 1994, Pat. No. 5,858,003.

[51] Int. Cl.⁷ .................................................. A61M 29/00
[52] U.S. Cl. ............................ 604/96; 604/99; 604/100; 606/192; 606/193
[58] Field of Search ............. 604/96–102; 606/192–194

[56] References Cited

U.S. PATENT DOCUMENTS

| | | | |
|---|---|---|---|
| 3,477,438 | 11/1969 | Allen et al. . | |
| 3,720,199 | 3/1979 | Rishton et al. . | |
| 3,875,939 | 4/1975 | Bolduc et al. ........................... | 128/235 |
| 4,237,935 | 12/1980 | Delmonte et al. ...................... | 137/860 |
| 4,432,758 | 2/1984 | Finegold ................................. | 604/104 |
| 4,491,126 | 1/1985 | Cullor .................................... | 128/1 R |
| 4,585,435 | 4/1986 | Vaillancourt ............................. | 604/27 |
| 4,598,579 | 7/1986 | Cummings et al. ....................... | 73/37 |
| 4,685,905 | 8/1987 | Jeanneret nee Aab ................. | 604/247 |
| 4,701,160 | 10/1987 | Lindsay et al. ........................... | 604/53 |
| 4,834,705 | 5/1989 | Vaillancourt ............................. | 604/83 |
| 4,998,914 | 3/1991 | Wiest et al. ............................... | 604/67 |
| 5,049,132 | 9/1991 | Shaffer et al. .......................... | 604/101 |
| 5,084,015 | 1/1992 | Moriuchi ................................. | 604/96 |
| 5,092,846 | 3/1992 | Nishijima et al. ...................... | 604/165 |
| 5,112,303 | 5/1992 | Pudenz et al. ............................ | 604/49 |
| 5,122,122 | 6/1992 | Allgood ................................... | 604/174 |
| 5,176,662 | 1/1993 | Bartholomew et al. ................ | 604/283 |
| 5,250,029 | 10/1993 | Lin et al. ................................. | 604/96 |
| 5,250,069 | 10/1993 | Nobuyoshi et al. ..................... | 606/192 |
| 5,279,583 | 1/1994 | Shober, Jr. et al. ..................... | 604/198 |
| 5,290,244 | 3/1994 | Moonka .................................. | 604/164 |
| 5,290,249 | 3/1994 | Foster et al. ............................ | 604/174 |
| 5,304,123 | 4/1994 | Atala et al. ............................... | 604/54 |
| 5,312,362 | 5/1994 | Pfolsgraf et al. ....................... | 604/167 |
| 5,334,170 | 8/1994 | Moroski .................................. | 604/80 |
| 5,459,700 | 10/1995 | Jacobs . | |
| 5,486,195 | 1/1996 | Myers et al. ............................ | 606/213 |
| 5,749,845 | 5/1998 | Hildebrand et al. . | |

FOREIGN PATENT DOCUMENTS

| | | |
|---|---|---|
| 0297723 | 5/1988 | European Pat. Off. . |
| 2290236 | 6/1994 | United Kingdom . |
| WO 82/03557 | 10/1982 | WIPO . |
| WO 92/13591 | 8/1992 | WIPO . |
| WO 93/10723 | 6/1993 | WIPO . |
| WO 96/27406 | 9/1996 | WIPO . |

OTHER PUBLICATIONS

Hu, H. et al., "Full–Load Expansion Technique and Preliminary Clinical Application", *Plastic and Reconstructive Surgery*, vol. 93 (7), pp. 1459–1464 (1994);.

Keller, W. et al., "Rapid Tissue Expansion for the Development of Rotational Skin Flaps in the Distal Portion of the Hindlimb of Dogs: An Experimental Study", *Veterinary Surgery*, vol. 23 (1), pp. 31–39 (1994);.

Lailas, N. et al., "Progressive Ureteral Dilation for Subsequent Ureterocystoplasty", *The Journal of Urology*, vol. 156, pp. 1151–1153 (1996);.

Magovern, J. et al., "A Permanent Arterial Access System", *ASAIO Transactions*, vol. 34 (3), pp. 460–462 (1988);.

Spodnick, G. et al., "Controlled Tissue Expansion in the Distal Extremities of Dogs", *Veterinary Surgery*, vol. 22 (6), pp. 436–443 (1993);.

Wigness, B. et al., "Bidirectional Implantable Vascular Access Modality", *Transactions American Society for Artificial Internal Organs*, vol. 28, pp. 54–57 (1982).

*Primary Examiner*—Mark Bockelman
*Attorney, Agent, or Firm*—Thomas J. Engellenner; Nutter, McClennen & Fish, LLP

[57] ABSTRACT

The present invention relates generally to the treatment of volume deficiency disorders of body structures and related syndromes, and more particularly to devices that deliver fluid at a controlled pressure into a balloon situated within or adjacent a body cavity to effect tissue expansion. The invention also provides methods for expanding volumetrically deficient structures. Methods of delivering fluid at a controlled pressure into an inflatable balloon are also disclosed.

5 Claims, 2 Drawing Sheets

SYSTEMS AND METHODS FOR PROMOTING TISSUE GROWTH

CROSS-REFERENCE TO RELATED APPLICATIONS

This application is a continuation-in-part of U.S. Ser. No. 08/326,711, entitled "Systems and Methods for Promoting Tissue Growth," filed on Oct. 20, 1994, now U.S. Pat. No. 5,858,003 the disclosure of which is incorporated herein by reference.

BACKGROUND OF THE INVENTION

The present invention relates generally to the treatment of volume deficiency disorders and syndromes, and more particularly to devices that deliver fluid at a controlled pressure into an interstice of a patient to effect tissue expansion and growth of the surrounding tissue, and to surgical procedures for augmenting volumetrically deficient natural body structures or for reconstructing damaged natural body tissue by attachment of tissue segments cultivated by tissue expansion. Methods of delivering fluid at a controlled pressure into an interstice are also disclosed.

Biological volume deficiencies, such as short gut syndrome, are persistent conditions that result when the volumetric capacity of a natural body structure, such as a bladder or a lung, is insufficient to allow the organ to operate effectively or at all. Additionally, the lack of volumetric capacity can create internal fluid pressures or body fluid reflux that damages other organs and tissue. Among the many causes of such deficiencies are birth defects and abdominal trauma.

Presently, the afflicted population receives surgical treatment, typically in the form of augmentation procedures that increase volumetric capacity of the body structure by rebuilding the structure in a procedure that attaches a flap of additional tissue to the afflicted structure. For example, an infant born with insufficient bladder capacity can receive a bladder augmentation in a procedure that typically rebuilds the infant's bladder by attaching a flap of gastrointestinal tissue to the bladder wall. The surgeon attaches the gastrointestinal tissue to the bladder wall in a manner that increases the surface area of the surrounding wall and thereby increase the volumetric capacity of the bladder. Generally, the surgeon selects gastrointestinal tissue because this tissue normally is available in sufficient amounts within the patient to provide the needed tissue for the augmentation procedure Although these procedures can be successful at relieving volumetric capacity deficiency, the complications that arise from attaching different tissue types can be severe and persistent. For example, with respect to bladder augmentation by attachment of gastrointestinal tract, the resulting complications for any patient can include lithiasis, metabolic complications, increased mucous production, increased infections, perforations and even malignant growths within the treated body structure. It is generally understood by the medical community that these complications can arise due to the attachment of a tissue type that lacks sufficient compatibility with the natural tissue of the body structure. Furthermore, bladder augmentation requires invasive surgical procedures which can cause patient discomfort and may require extended times for recovery.

SUMMARY OF THE INVENTION

The present invention provides systems and methods for promoting the growth or expansion of biological tissue, thereby increasing the volumetric capacity of a natural body structure. Tissue portions (e.g., which have been surgically resected from the expanded body structure) can also be used in reconstructive surgery. In particular, the present invention provides methods for promoting progressive tissue growth for bladder expansion. To this end, the present invention discloses systems and methods that introduce a pressurized fluid within a body structure, such as a urinary bladder, of a patient. The pressurized fluid causes the surrounding tissue to expand and thereby creates a condition that is generally understood to promote tissue growth. The expansion of the body structure can substantially relieve the condition of volume deficiency.

As used herein, the term "tissue expansion" is intended to encompass dilation of natural body lumens, stretching of tissue segments and promotion of new tissue growth in response to an applied pressure. The term "volume deficiency" is intended to encompass disorder and syndromes related to deficient volumetric capacity of a space or gap between tissue or within a natural body structure and includes by way of example, short gut syndrome and bladder volume insufficiency.

"Interstitial cavity," as the term is used herein, encompasses interstices in a tissue or structure of a natural body structure, spaces and gaps existing between layers of tissue or existing within organs, and can include interstices within the interior of the ureter, bladder, intestines, stomach, esophagus, trachea, lung, blood vessel or other organ or body cavity, and will be further understood to include any surgically created interstice that defines an interior cavity surrounded by tissue.

The term "injection port," as used herein, refers to an element adapted for introduction of a fluid under pressure. Preferably, an injection port is adapted for pressure-tight connection to a catheter and provides a pressure-tight connection to a source of fluid under pressure. Injection ports suitable for use in the systems and methods of the invention are known in the art and include, but are not limited to, septa (which can be self-sealing), adapters such as threaded nipples or Luer-type adapters, and the like.

In one aspect, the present invention encompasses devices for delivering fluids under pressure to an interstitial cavity (e.g., the urinary bladder) within a patient. Generally, the devices include an inflatable balloon, a catheter element that couples a source of fluid under pressure into fluid communication with the inflatable balloon, and a valve element that is adapted to restrict the flow of the fluid to a select direction of flow and thereby prevent back flow of fluid. The balloon is preferably dimensioned for placement within an interstitial cavity, e.g., the balloon is selected such that the balloon will exert pressure on a tissue wall such that tissue expansion is promoted. The catheter element includes a first lumen for flowing the fluid under pressure into the balloon. The catheter preferably includes at least one drain opening at or near a distal end of the catheter, drainage means (e.g., a body fluid collection element such as a drainage bag) secured to a proximal end of the catheter, and a second catheter lumen in fluid communication with the drain opening and the drainage means, for drainage of a body fluid from the body cavity to the drainage means. Although in a preferred embodiment a single catheter is preferred (which catheter can include a plurality of lumens), it will be understood that the invention also contemplates the use of a plurality of catheter elements (e.g., each catheter having a single lumen) for providing a fluid under pressure and providing a drainage path for a body fluid.

In a preferred embodiment of the invention, the fluid delivering devices further include a pressure release element that reduces fluid pressure within the interstitial cavity by releasing fluid responsive to a user-selected fluid pressure limit. One realization of the pressure release element can be as a release port element that is arranged in fluid communication with the first lumen of the catheter element, and therefore, the fluid within the first catheter lumen, and that further includes a release plug that fluidicly seals the release port to maintain fluid in the first catheter lumen as long as the fluid pressure is below a predefined threshold pressure, and that is adapted to disengage from the release port responsive to the fluid in the first catheter lumen, or in the balloon or interstitial cavity, reaching the threshold fluid pressure limit.

In a particularly preferred embodiment, the fluid delivering devices of the invention can be configured for indwelling placement in a patient's body. For example, the catheter element of a device of the invention can be dimensionally adapted for indwelling placement within the urethra and bladder of the patient, such that the balloon, when expanded, substantially fills the patient's bladder. The catheter element can include a drain opening near the distal end portion of the catheter, for draining urine from the bladder. The urine thus drained from the bladder can be flowed through a second catheter lumen to a urine collection element, such as a bag, which can be disposed outside the patient's body for ready collection and disposal of the urine.

The catheter element is adapted for conveying fluid under pressure to the balloon. The catheter element can include a silastic catheter tube that has a portion dimensionally adapted to fit within an interstitial lumen, such as the ureter. Depending upon the application, the catheter can be a short or long section of, e.g., silastic tube or other polymeric tubing, that extends from an injection port and has the valve element incorporated therein. The catheter clement is preferably sized to permit insertion and placement of the catheter (and the attached balloon), into the urethra and bladder, through a standard cystoscope.

The catheter can connect to a port element that can include an injection port that has an elastic septum adapted for maintaining a fluid under pressure within the catheter element. The port can connect to a pump element that provides a source of fluid at a selected pressure.

In another embodiment, the present invention can be realized as a fluid delivery system that a catheter element for conveying the fluid to the interior of the cavity, a balloon secured to a distal end of the catheter, an injection port element secured to a proximal end of the catheter element that fluidicly couples the pump element with the catheter element, and a valve element that restricts the direction of fluid flow thereby preventing a back flow of pressurized fluid escaping through the injection port. The catheter element includes a first lumen for flowing a fluid under pressure into the balloon. The catheter preferably includes at least one drain opening at or near a distal end of the catheter, a body fluid collection element secured to a proximal end of the catheter, and a second lumen in fluid communication with the drain opening and the fluid collection element, for drainage of a body fluid from an interstitial cavity to a drainage device at a proximal end of the catheter. The apparatus can further include a pump element for providing a source of fluid under pressure.

In one embodiment, the pump element can comprise a syringe element that has a reservoir of fluid in fluid communication with a pressure sensor element, such as a manometer element, to indicate the pressure of fluid being introduced into the balloon. The hollow needle of the syringe element can penetrate the septum, and the septum can elastically form a pressure resistant fluid-tight seal around the penetrating needle. By action of the syringe piston, the fluid in the syringe reservoir is placed under sufficient pressure to introduce fluid into the catheter element and thereby into the balloon in the interstitial cavity. The pressure sensor in fluid communication with the fluid reservoir responds to the pressure of the fluid introduced into the catheter and thereby provides a report of the fluid pressure introduced into the balloon. Thus, the pump element can be adapted to allow the selective control of the fluid pressure provided to the balloon, and thereby control the pressure exerted by the balloon upon the tissue wall of the body cavity in which the balloon is situated.

In another embodiment, the pump element can include a motorized pump clement, a fluid reservoir and a control element that includes a manometer or other pressure sensor in fluid communication with the fluid within the catheter element and a control circuit that responds to the measured fluid pressure to controllably operate the pump to maintain the proper fluid pressure within the balloon. In a further embodiment, the control element can include a processing unit that operates the motor pump to vary selectively over time the fluid pressure within the balloon. Preferably, the pump element has a mounting clement for removably and replaceably mounting to the injection port element for selectively forming fluid communication with the catheter element.

The injection port element is adapted for fluidicly coupling the pump element to the catheter element and can be integrally formed with the valve that is adapted to prevent pressurized fluid within the catheter from back flowing and escaping through the injection port element. The injection port can have a mounting element that is adapted for removably and replacably coupling in fluid communication to the pump element. The mounting element can be a threaded nipple, a latch or any other coupling that can form a pressure resistant fluid seal. In one embodiment, the injection port element can be an injection port that is adapted for subcutaneous implantation within a patient or for transcutaneous attachment to a patient.

The balloon can be secured to a distal end of the catheter element by a variety of means, some of which are known in the art. The balloon and catheter may be formed integrally or unitarily, or may be bonded together. The balloon, in an uninflated or collapsed state, can be positioned substantially surrounding the outer surface of the catheter element, as is conventional for balloon catheters. Alternatively, the uninflated or collapsed balloon can be positioned within a recess at the distal end of the catheter. The balloon can be inflated in response to a supply of fluid under pressure through the first catheter lumen, and in an inflated state extends outwardly from the recess in the catheter end to fill the body cavity. In the collapsed condition, the balloon can be dimensionally adapted for fitting within the body cavity to be dilated, and in the inflated condition can be dimensionally adapted to volumetrically substantially fill the body cavity and thereby forcibly cause the tissue wall surrounding the cavity to stretch or expand. Additionally, the balloon element can be dimensionally adapted to extend into the interstitial cavity a select distance and thereby contact, in the inflated condition, only a portion of the interstitial cavity to promote tissue expansion in a select section of the surrounding tissue wall. The balloon surface can further include vertical ridges or channels or protrusions that facilitate drainage of body fluids from the body cavity undergoing expansion.

Fabrication of inflatable balloons is well known in the art. The balloon element is preferably adapted to contain the fluid and thereby prevent fluid from entering the body cavity being dilated. The catheter and balloon may be fabricated using a bactericidal-containing synthetic resin, coated with bactericidal or friction-reducing agents, or the balloon may be inflated with a bactericide-treated fluid. In certain embodiments, the fluid is a saline solution, and preferably contains an antibacterial agent. In certain preferred embodiments, the fluid can be a gas, such as compressed air or an inert gas such as nitrogen.

The device can additionally include a pressure release element that reduces fluid pressure by releasing fluid from within the balloon or first catheter lumen. The pressure release element can include a valve and pressure sensor disposed within the pump element, to measure the fluid pressure of the fluid provided to the first catheter lumen and to deactivate the pumping element in response to a fluid pressure within the catheter when the pressure exceeds a selected maximum pressure or to release fluid from within the catheter by action of the valve element.

In another aspect of the invention, methods are disclosed for treating volume deficiency disorders of a body structure by expanding, enlarging, or inflating a volumetrically deficient body structure. The methods employ a tissue dilation system that comprises a source of fluid under a select pressure, an inflatable balloon, a catheter element for carrying the fluid under pressure to the balloon, and a valve element for restricting said fluid under pressure to a select direction of fluid flow. The method further includes the steps of introducing the inflatable balloon into the volume deficient body structure and introducing fluid into the balloon to dilate a tissue wall of the body structure to cause tissue expansion (e.g., by promoting tissue growth), such that the volume deficiency disorder is treated, i.e., the volume of the body structure is increased.

In a preferred practice, the method also includes the steps of monitoring the fluid pressure within the interstitial cavity, and releasing fluid from the interstitial cavity responsive to a select pressure level, to reduce the fluid pressure within the interstitial cavity.

In a further preferred practice of the invention, fluid under pressure is introduced into an interstitial cavity during select intervals, such as by daily or weekly introductions, to promote progressive tissue growth over a selected period of treatment. In one practice, saline fluid, preferably including an antibacterial agent, can be introduced daily into a balloon disposed within a body cavity (e.g., a bladder) and thereby promote tissue expansion and growth thereof. The daily fluid introduction can be maintained for a period of thirty days or, more preferably, until the tissue wall has expanded sufficiently to alleviate a volume deficiency disorder. Alternatively, the fluid pressure within the balloon can be monitored, preferably in connection with a control element on the pump. The control element can operate the pump to maintain a selected pressure within the balloon.

In one practice of the invention, the step of preparing a portion of an interstitial cavity includes selecting an interstitial cavity that has a wall of tissue phenotypically compatible with the volumetrically deficient cavity.

The term "phenotypically compatible tissue" as used herein, encompasses tissues that have similar tissue phenotype, similar gross cellular characteristics, can be similarly differentiated, histologically similar, such as having compatible epithelial linings, or derived from the same or similar embryonic structures.

In another aspect of the present invention, methods are provided for expanding tissue to promote tissue growth. The method includes the step of introducing fluid under a select pressure into a balloon disposed within an interstitial cavity by providing a pump element for providing fluid at a select pressure, fluidicly coupling a catheter element between the pump element and the balloon, providing a valve element within the catheter that prevents flow back by restricting the introduction of fluid to a select direction of fluid flow, and sealing fluid-wise the balloon to the catheter element.

DETAILED DESCRIPTION OF ILLUSTRATED EMBODIMENTS

The present invention provides systems and methods for expanding tissue or promoting the growth of biological tissue by introducing a pressurized fluid within a body cavity or interstice of a patient.

To this end, the present invention encompasses fluid delivery systems that include an inflatable balloon, a catheter element for coupling to a source of fluid under pressure and for delivering the fluid to the balloon, and a valve element that restricts the direction of fluid flow thereby preventing back flow of pressurized fluid from escaping through the port.

Figure 1:
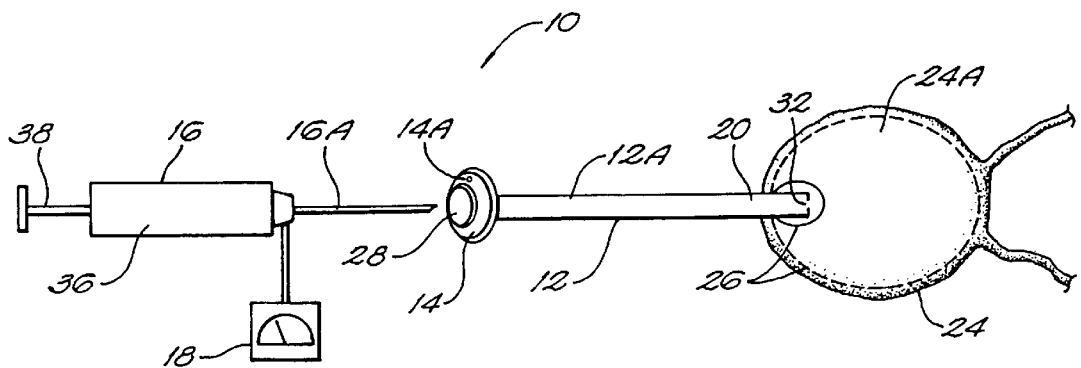
FIG. 1 illustrates one embodiment of the present invention for introducing fluid at a select pressure into a balloon disposed within an interstitial cavity.

FIG. 1 illustrates a system 10 constructed according to the present invention for delivering fluids at a select pressure into a balloon 26 disposed within an interstitial cavity 24A. The system 10 includes a catheter element 12 that has a port element 14 with an optional safety release element 14A, a valve element 28, a pump element 16 having a manometer 18, and an exit port 22 in catheter 12.

As illustrated in FIG. 1, the distal portion 20 of catheter element 12 is dimensionally adapted for fitting within the body cavity 24A of a body structure 24 (e.g., a bladder). The fluid exit port 22 in the distal end 20 is in fluid communication with a hollow passage 12A that extends through the catheter element 12 which fluidicly couples with the port element 14. The port element 14 in the illustrated embodiment includes an elastically deformable septum 28 that can be penetrated by a needle element 16A of the syringe pump element 16 illustrated in FIG. 1. The syringe pump element 16 illustrated includes a fluid reservoir 36 that contains a fluid, such as saline solution. Therefore, FIG. 1 illustrates a device that fluidically couples balloon 26 within an interstitial cavity, such as the cavity 24A, to a reservoir 36 of fluid under pressure for delivering into the balloon 26 at a select pressure. The device illustrated in FIG. 1 is suitable for implanting in the patient's body, e.g., through a surgically-created opening; the port element 14 can be subcutaneously placed, providing a fully implantable system 10.

In the illustrated embodiment of FIG. 1, the catheter element 12 is a silastic catheter adapted for being subcutaneously inserted within a patient during the tissue expansion process. An exit port 32 extends through the distal end 20 of the catheter 12 to provide a fluid path into the balloon 26. In the illustrated embodiment, the distal end 20 of the catheter element 12 is dimensionally adapted for inserting into the lumen 24A of the a natural body cavity such as the bladder. At the proximal end of the catheter element 12, the catheter is connected to a port element 14 that includes the valve element 28. Preferably, the catheter element 12 is coupled to the port element 14 in a pressure resistant fluid tight manner that maintains a seal between the catheter element 12 and the port element 14 when the catheter element 12 is filled with fluid under pressure. The proximal end portion can be a separately manufactured element that couples to a catheter element 12 with a pressure resistant fluid tight seal that maintains a sealed connection between the catheter element 12 and the proximal end element when the catheter element 12 contains fluid under pressure. The catheter element 12 can be any of the silastic catheter elements that are sufficiently pressure resistant to contain fluid at the pressure level appropriate for the particular application.

In the illustrated embodiment, the system is used to promote tissue expansion of the bladder 24A. In one practice of this application, the system 10 introduces fluid into the balloon 26, e.g., at a pressure of between about 8–20 inches of water. The catheter element 12 can be dimensionally adapted to frictionally engage a body wall, e.g., urethral or bladder wall 24.

FIG. 1 further illustrates an optional safety release seal element 14A. The illustrated safety release element can be integrally formed with the port element 14, and includes a fluid channel (not shown) that connects the safety release seal to the fluid within the catheter 12. The illustrated seal element 14A has a plug element frictionally engaged within a port that couples in fluid communication with the integrally formed fluid channel. The plug element can be fitted into the port so that the plug disengages from the port when the fluid under pressure reaches a maximum pressure. The disengaged plug allows fluid to escape from the catheter, and therefore reduces pressure within the balloon 26.

Figure 2A:
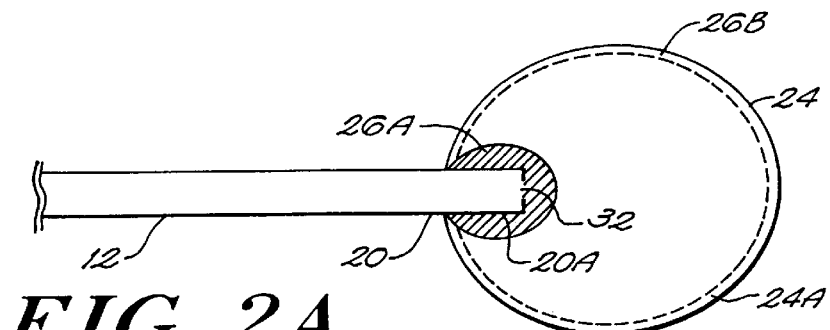
FIGS. 2A–2B illustrate certain means of securing a balloon to a catheter element of the inventive devices.
Figure 2B:
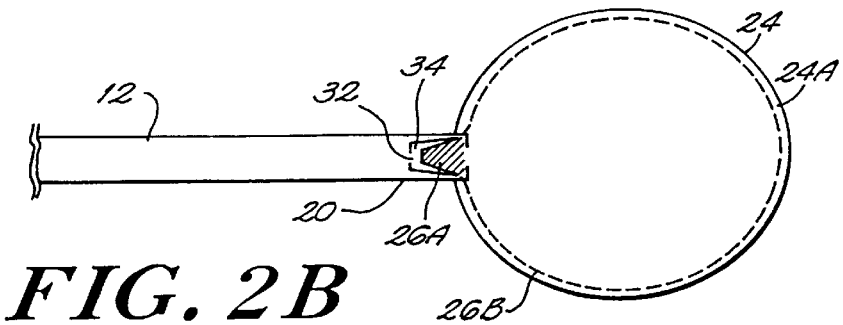

With reference to FIGS. 2A–2B, alternative structures for balloon attachment can be described. FIG. 2A illustrates a balloon 26 which, in an uninflated or collapsed condition 26A, is disposed on an outer surface 20A of the distal end of the catheter 12. The balloon can be folded or rolled to minimize the cross-sectional size of the balloon. The distal portion of the catheter element is inserted into the body cavity 24 so that the uninflated balloon 26 is disposed within or adjacent the interior of the cavity 24A. The balloon fluidically communicates with catheter 12 through an opening 32 at or near the catheter tip. The balloon is then inflated to an inflated state 26B (shown in phantom) in response to a fluid pressure to volumetrically fill at least a portion of the bladder to engage the bladder wall and cause expansion of the bladder volume. The balloon surface can further include vertical and/or horizontal ridges or channels, or protrusions that facilitate drainage of body fluids from the bladder (or other body cavity) undergoing expansion.

FIG. 2B illustrates an alternative embodiment of balloon attachment to the catheter 12 The balloon 26, in an uninflated or collapsed state 26A, is wholly or partially disposed within a recess 30 in the distal end of catheter 12. The uninflated balloon can be folded or rolled to decrease the volume occupied by the uninflated balloon. In this way, the cross-sectional area of the catheter element can be minimized, providing easier handling and insertion, and reducing the possibility of damage to the uninflated balloon, or to surrounding tissue, during insertion of the catheter into the patient's body. The balloon fluidically communicates with catheter 12 through an opening 32 at or near the catheter tip. As described above, the distal portion of the catheter element is inserted into the body cavity 24A so that the uninflated balloon 26 is disposed within or adjacent the interior of the cavity 24A. The balloon is then inflated to an inflated state 26B (shown in phantom) in response to a fluid pressure to volumetrically fill at least a portion of the bladder to engage the bladder wall and cause expansion of the bladder volume.

Referring again to FIG. 1, the port element 14 illustrated in FIG. 1 can be an injection port that has a valve 28 formed from a septum integrally constructed into the port element 14. The septum valve 28 can be an elastic membrane of the type commonly used in subcutaneously implanted injection ports and being a self-sealing membrane that forms a pressure resistant fluid seal around a needle element such as the hypodermic needle element 16A illustrated in FIG. 1 as penetrating the septum. By providing a septum valve 28 that seals about a needle element 16A with sufficient strength to prevent fluid contained under pressure within the catheter element 12 from escaping through the septum wall, the valve element 28 restricts fluid under pressure to a select direction of flow as it is introduced through the needle 16A into the catheter element 12, and thereby prevents flow back. In an alternative embodiment, the port element 14 can be a fitting or connector, such as a Luer connector, suitable for coupling to a source of fluid under pressure (e.g., a pump).

The pump element 16 illustrated in FIG. 1 is a syringe that has a needle element 16A adapted for carrying a fluid, a pressure sensor element 18, a fluid reservoir 36 and a piston element 38. The pressure sensor can be a manometer element 18 that couples in fluid communication to the fluid within the reservoir 36 and can indicate the pressure of the fluid within the reservoir 36 being injected into the catheter element 12, and thereby indicate the pressure of the fluid within the balloon 26. In operation, the piston element 38 is depressed into the fluid reservoir 36 to place the fluid under pressure and to inject the fluid through the hollow needle element 16A that has penetrated through the valve element 28. The septum valve 28 comprises a thickened portion of, preferably a silicone elastomer material having characteristics which permit repeated, intermittent puncture by a needle 16A for injecting fluid at a select pressure from the fluid reservoir 36. Such a needle 16A is preferably 20 gauge or smaller.

Figure 3:
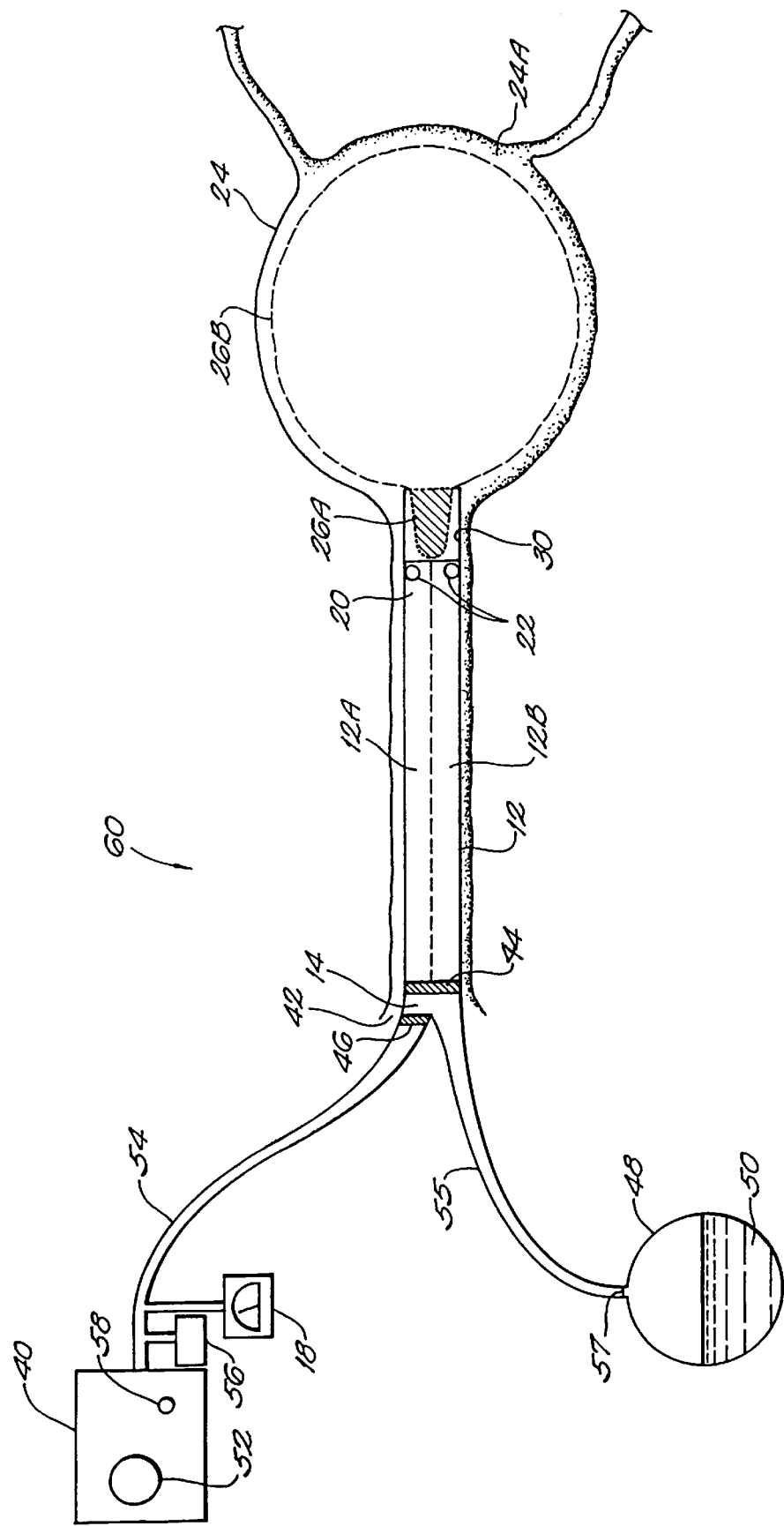
FIG. 3 illustrates an alternative embodiment of the present that includes a motorized pump element and a control element that operates the pump to selectively control the pressure of fluid introduced into the balloon.

FIG. 3 illustrates a system 60 that represents an alternative embodiment of the present invention. System 60 includes the port element 14, catheter 12, and balloon 26. The catheter 12 has a first lumen 12A which is in fluid communication with the balloon 26 and with a source of compressed air 40, through valve element 44. Valve element 44 can be any one-way valve adapted for retaining a fluid under pressure within the system, including check valves and the like. The one-way valve element illustrated in FIG. 3, fluidicly seals the fluid deliver system to thereby prevent fluid (e.g., compressed air) from escaping from the balloon. The illustrated one-way valve 44 is merely one check valve that can maintain a closed condition responsive to fluid pressure in order to fluidicly seal a balloon maintaining a fluid under pressure. It should be apparent to one of ordinary skill in the art that other one-way valves, check valves, and other pressure containment elements can be practiced with the present invention without departing from the scope thereof and it is considered to be within the skill of one of ordinary skill in the art to provide alternative one-way valve elements.

The source of compressed air 40 is preferably removably and replacably mounted to the port element 14 by convention means, e.g., through a Luer connector or by threaded engagement with the coupling element 46 to provide a pressure resistant, air-tight seal between a pumping element 40 and the device 60. Fluid (e.g., compressed air) at a select pressure is provided by the pumping element and introduced into the catheter element 12 (through lumen 12A) via port 14 and thence to the balloon 26.

In the embodiment of FIG. 3, the catheter element 12 has a plurality of drain openings 22 located near a distal end 20 of the catheter element 12 and adapted for draining a body fluid from the body cavity 24A. The drain openings 22 are in fluid communication with a second catheter lumen 1 2B which fluidically communicates with the body fluid collection element 48, which in the illustrated embodiment is a drainage bag for containing urine 50. The drain openings 22 can be of a size sufficient to permit drainage of a body fluid, such as urine, at a rate effective to prevent excessive buildup of body fluid within the cavity 24A. First catheter lumen 1 2A and second catheter lumen 12B can be disposed concentrically within catheter 12 (e.g., catheter 12 is a double wall catheter), or can be separated by a wall partition, as shown in phantom in FIG. 3. In a preferred embodiment, lumen 12B has a greater cross-sectional area than does lumen 12A, to provide for efficient drainage of the body fluid from the body cavity. Selection of an appropriate means for providing lumens 12A and 12B will be routine for one of ordinary skill in the art.

The device 60 illustrated in FIG. 3, has a catheter element 12 that can slidingly insert through the urethral opening 42 into the bladder. As described above, drain openings 22, in fluid communication with catheter lumen 12B and body fluid collection receptacle 48, permit the removal of body fluids such as urine. In a preferred embodiment, the fluid collection receptacle is removably and replaceably secured in fluid-tight relationship to catheter 55, e.g., through attachment means 57. Removable, and preferably disposable, bags for collecting urine are well known in the art. Thus, placement of the system of FIG. 3 does not require invasive surgical procedures and is suitable for transurethral placement for extended time periods.

FIG. 3 further illustrates means for delivering and maintaining fluid under pressure within a body cavity 24A. The pumping assembly 40 illustrated in FIG. 3 includes a pressure indicator 18, a motor assembly 52, a connecting lumen 54 that includes a pressure release valve 56, and pressure control knob 58.

The illustrated pumping element 40 can be any conventional air pumping element for providing a source of air under a select pressure. The pumping element 40 can be a peristaltic pump or any other conventional pumping system. The motor assembly 52 is an electric motor pump that moves air through the fluid delivery lumen 54, past the port 14, through catheter 12 and into the balloon 26. In one embodiment, the pressure indicator gauge 18 measures the pressure of air being pumped into the balloon 26. The fluid pressure can be selectively controlled by an operator, by adjusting the control knob 58 that connects to a control element within the pump assembly 40 that controls the pumping motor 52 to establish a select fluid pressure for the fluid being pumped. The control element receive input from manometer 18 that measures the fluid being forced through the lumen 54 and into the balloon 26. The pump control element can be electrical circuit card assembly having a processing unit, data memory and program memory. The control element can operate in response to a program of processing unit instruction codes, to respond to the measured fluid pressure to maintain the selected pressure level, to deactivate the pump if a maximum pressure limit is reached, or to open the pressure release valve 56 if a maximum pressure is exceeded. If desired, a feedback lumen (not shown) can be provided to communicate a pressure in the balloon 26 to manometer 18, to directly measure the pressure in balloon 26.

In another aspect, the present invention includes methods for promoting progressive tissue growth, e.g., for such as expanding volumetrically deficient body structures.

In one practice of the methods of the invention, the distal portion of a fluid delivery system of the invention (e.g., system 10 of FIG. 1 or system 60 of FIG. 3) is inserted within a body cavity such as the bladder. In practice, fluid is delivered through the catheter into the balloon at a select pressure. Preferably, the fluid is introduced into the balloon in intervals in order to progressively promote tissue growth. As the wall of the interstitial cavity expands due to the force of pressure against the wall, the fluid pressure may diminish within the balloon, with a corresponding decrease in the force exerted against the cavity wall. At subsequent intervals, more fluid can be introduced into the balloon. Alternatively, in one practice of the invention, the device continuously delivers fluid into the balloon each time fluid pressure is detected below a selected pressure level.

Once the tissue wall has expanded sufficiently, the balloon can be deflated and the device removed from the patient's body.

The invention will next be described in connection with a non-limiting experimental protocol.

EXAMPLE

The complications associated with bladder augmentation using the gastrointestinal tract are well known. These include malignancy, lithiasis, metabolic complications, increased mucus production, increased infections, and perforation. We have designed a system wherein progressive dilation can be performed in a bladder to gradually increase bladder volume.

A catheter device of the invention was inserted through the urethra of a female human patient (aged about 15 years) suffering from bladder volume insufficiency. The starting bladder volume was about 15 ml. The balloon was then inflated with compressed air over a period of about one hour. Balloon expansion continued until the patient indicated increasing discomfort. Balloon inflation was halted, and the pump was uncoupled; a valve maintained the fluid pressure within the balloon catheter system. The patient reported little subsequent discomfort and was not hospitalized (a urine collection bag can collect urine (through drain openings in the catheter) while the catheter remains in position, if desired). The system was then removed. The total bladder volume after the expansion procedure was about 80 ml. Thus, the bladder volume was significantly increased after only a single session of expansion, with minimal patient discomfort and surgical intervention.

This system can also be used to dilate and expand growth of tissues in other organ systems where tissue shortage is present. Patients with a short gut syndrome who are born with or acquire a limited amount of gastrointestinal tract, would also be ideal candidates for this technology. Currently, some patients with the short gut syndrome have no therapeutic recourse and die. The system of tissue dilation and expansion could also be used for patients with inadequate lung volume either to congenital or acquired conditions. These patients usually require extracorporeal membrane oxygenation (ECMO), which in of itself, carries an 80% mortality. Hydraulic tissue expansion could be performed through the trachea with a similar device into an individual lung organ while the patient is on ECMO. This system could also be utilized to expand individual blood vessels which could later be used for any type of vascular bypass surgery as graft material, such as that needed in aorto-femoral surgery, thereby avoiding the need for artificial materials such as polytetrafluoroethylene (Teflon) grafts, which are associated with various complications. This system could also be used for local tissue expansion, such as for skin or scalp areas, e.g., where additional integument is needed for reconstructive purposes. This system could be further used for bladder augmentation, urethral dilation, ureteropelvic junction obstruction repair, ureterovesical junction obstruction repair, repair of ureteral, urethral, or bowel strictures, or any area in the body where an obstructive process occurs due to strictures, adynamic segments, or lack of tissue or volume. Other organs which can be expanded with the systems and methods of the invention include vagina, uterus, Fallopian tubes, and the like. This system could also be for gastric dilation, expansion of tracheal tissue, esophageal enlargement, intestinal expansion, and any area where dilation or tissue expansion is required.

The present invention has been described with reference to certain illustrated embodiments. However, those skilled in the art will recognize, or be able to ascertain using no more than routine experimentation, many equivalents to the specific embodiments of the invention described herein. The invention and such equivalents are to be understood and determined by reference to the following claims.

I claim:

1. An apparatus for delivering fluid under pressure to a balloon to promote tissue expansion, the apparatus comprising:

a catheter element;

an inflatable balloon secured to and in fluid communication with a distal end of the catheter element and adapted for placement within a body cavity;

an injection port secured to and in fluid communication with a proximal end of the catheter element;

a valve element that prevents backflow out of said injection port; and pressure release means for reducing fluid pressure within the balloon by releasing fluid if the pressure exceeds a predefined level, the pressure release means including a release port element arranged in fluid communication with the catheter element and further including a release plug that fluidicly seals the release port and is adapted for disengaging from the release port responsive to a user-selected fluid pressure limit.

2. The apparatus according to claim 1 wherein, the catheter element comprises a silastic catheter dimensionally adapted for placement within a urethra of a patient.

3. The apparatus according to claim 1 wherein, the valve element is disposed within the injection port and further comprises a septum adapted to elastically form a seal around a hypodermic needle.

4. The apparatus according to claim 1 wherein, the injection port is adapted for subcutaneous insertion within a patient.

5. The apparatus according to claim 1 wherein, the catheter means is arranged for replacably and removably coupling to a source of fluid pressure.

* * * * *